US006352702B1

(12) United States Patent
Ryan et al.

(10) Patent No.: US 6,352,702 B1
(45) Date of Patent: Mar. 5, 2002

(54) ANTIMICROBIAL COMPOSITION

(75) Inventors: Robert Eugene Ryan; Sandra Morris, both of Norfolk (GB)

(73) Assignee: Barrier Biotech Limited, Norfolk (GB)

( * ) Notice: Subject to any disclaimer, the term of this patent is extended or adjusted under 35 U.S.C. 154(b) by 0 days.

(21) Appl. No.: 09/554,105

(22) PCT Filed: Nov. 30, 1998

(86) PCT No.: PCT/GB98/03573

§ 371 Date: May 26, 2000

§ 102(e) Date: May 26, 2000

(87) PCT Pub. No.: WO99/27793

PCT Pub. Date: Jun. 10, 1999

(30) Foreign Application Priority Data

Nov. 28, 1997 (GB) .............................................. 9725291

(51) Int. Cl.⁷ ................................................ A01N 25/02
(52) U.S. Cl. ...................... 424/405; 424/406; 424/742; 424/748; 424/770
(58) Field of Search .................. 424/742, 770, 424/748, 405, 78.07, 406

(56) References Cited

U.S. PATENT DOCUMENTS 5,629,281 A    5/1997  Butler 5,882,647 A  *  3/1999  Yoshpa .................... 424/195.1

FOREIGN PATENT DOCUMENTS

WO    WO 96 28033 A    9/1996

OTHER PUBLICATIONS

Database WPI Section Ch, Week 9421, Derwent Publications Ltd., London, GB, XP002095007 91.

J.C. Maruzzella & P.A. Henry, "The in vitro antibacterial activity of essential oils and oil combinations", J. Am. Pharm. Ass., 1958, XP002095004.

J.E.F. Reynolds (Ed.), "Martindale. The Extra Pharmacopoeia", 1993, The Pharmaceutical Press, London, XP002095006.

D.L.J. OPDYKE, "Fragrance Raw Materials Monographs. Clove bud oil", 1975, Food Cosmet. Toxicol., XP002095005.

* cited by examiner

*Primary Examiner*—Neil S. Levy
(74) *Attorney, Agent, or Firm*—Bacon & Thomas

(57) ABSTRACT

There is disclosed an antimicrobial composition comprising an antimicrobially effective amount of clove bud oil and two or more of eucalyptus oil, cajaput oil, lemongrass, lavender or tea tree oils. Use of the composition as a treatment for cold sores, head lice, vaginal thrush, verruca, warts, athletes foot, an antimicrobial mouth wash in addition to a surface cleaner are also disclosed.

20 Claims, No Drawings

ANTIMICROBIAL COMPOSITION

The present invention is concerned with an antimicrobial composition, and in particular with such a composition the active ingredient of which comprises natural or essential oils.

Essential oils have been used previously for use as antiviral or antibacterial agents. For example, clove bud oils have been previously described having antiseptic, antiviral and larvicidal capabilities.

The present inventors have surprisingly found that a composition having a particular blend of essential oils exhibits a particularly synergistic and broad spectrum antimicrobial effect, and which composition has never previously been described.

Therefore, according to a first aspect of the invention there is provided an antimicrobial composition comprising an antimicrobially effective amount of clove bud oil and two or more of eucalyptus oil, cajaput oil, lemongrass, lavender or tea tree oils. In one embodiment the antimicrobial composition comprises, by volume, approximately from 16 to 40% eucalyptus oil, 16 to 40% cajaput oil and 32 to 56% clove bud oil. The composition according to this embodiment is preferably diluted with water in which case the composition comprises preferably, from 10% to 15% eucalyptus oil, 10–15% cajaput oil, 15–25% clove bud oil, 2.5 to 7.5% surfactant and from 40 to 60% water. This composition is particularly advantageous in terms of its antimicrobial properties. Furthermore, the composition is particularly broad spectrum and is relatively non-toxic to mammals, particularly humans.

Preferably, the composition according to this embodiment comprises by volume, 12.5% eucalyptus oil, 12.5% cajaput oil, 20% clove bud oil, 5% surfactant and 50% water, or a deviation of from +or –10% in the quantity of each of the respective ingredients. In one embodiment the surfactant may comprise an anionic surfactant which may be selected from any of alkylarylsulfonates, alkanesulfonates, alcohol and alcohol ether sulfonates, polyether carboxylates, olefinsulfonates, -sulfomonocarboxylic esters and phosphorous containing anionic surfactants.

The composition according to the invention may advantageously be utilised for particularly harsh environments, such as for example, drains or the like. Alternatively, it may be diluted further in, for example, water and from anything up to 1 part disinfectant to 200 parts water for subsequent application to the area or locus of interest. Such a further dilution step is necessary where the composition is for human application.

One or more other ingredients may be optionally included in the composition of the invention in order to provide aesthetic or other beneficial properties thereto. Such ingredients may include for example, additional antimicrobial agents, deodorisers, colouring agents, fragrances, emulsifiers and the like. A further ingredient, such as anhydrous lanolin may be provided in an amount of from 10 to 20% by volume of the composition, where a cream based application is desired such as in an athletes foot cream. When such a lanolin is included the amount of water may be adjusted to an amount sufficient to make the composition 100% by volume.

Other essential oils may be included in the composition according to the invention.

The composition according to the invention may, advantageously be provided as for example, a powder or the like, for subsequent hydration and application to the locus of interest.

The composition according to the invention is particularly versatile and by virtue of its relative lack of toxicity to humans, can also be used for many human applications. For example, the composition of the invention may be used as a mouth wash, cold sore relief, in head lice control, to alleviate vaginal thrush, a verruca or wart treatment or to treat athletes foot. The composition has also been found to be a particularly effective disinfectant and antimicrobial surface cleaner.

According to a further aspect of the present invention there is provided use of a composition according to the invention in the preparation of a medicament to treat cold sores, head lice, vaginal thrush, verruca, warts, athletes foot or as an antimicrobial mouth wash. The mouth wash preferably comprises from 1 to 3% clove bud oil, 1 to 3% eucalyptus oil, 1 to 3% surfactant and 90 to 97% water. However, it even more preferably comprises 2% clove bud oil, 2% eucalyptus oil, 2% surfactant and 94% water. The cold sore preparation comprises from 10 to 30% clove bud oil, 5 to 15% tea tree oil but even more preferably approximately 20% clove bud oil and 10% tea tree oil with the remaining ingredient made up of water for blending into a cream.

The head lice composition comprises in approximate amounts from 2 to 6% eucalyptus oil, 1 to 3% cajaput oil, 2 to 6% clove bud oil, 2 to 4% surfactant and 81 to 93% water. Preferably, however, the composition comprises approximately 4%. eucalyptus oil, 2% cajaput oil, 4% clove bud oil, 3% surfactant and 87% water. The composition may preferably be further diluted to 1 part composition to 20 parts water. The vaginal thrush preparation preferably comprises approximately from 10 to 20% clove bud oil, 1 to 5% lavender oil, 2 to 8% tea tree oil, 3 to 7% surfactant and 65 to 85% water. Even more preferably however the composition comprises 15% clove bud oil, 3% lavender oil, 5% tea tree oil, 5% surfactant and 72% water.

The verruca preparation preferably comprises approximately from 10 to 30% clove bud oil, 5 to 15% cajaput oil, and 10 to 20% lemongrass oil. Preferably, the composition comprises 20% clove bud oil, 10% cajaput oil and 15% lemongrass, in a liquid base. The wart composition preferably comprises from 5 to 15% clove bud oil, 10 to 20% lemongrass oil, 2 to 8% tea tree oil, but even more preferably comprises approximately 10% clove bud oil, 15% lemongrass oil and 5% tea tree oil.

A surface cleaning formulation composition is also provided which preferably comprises 20 to 30% sea weed surfactant, 1 to 3% clove bud oil, 1 to 3% eucalyptus oil, 1 to 5% orange and 0.5 to 1.5% lemongrass, but even more preferably comprises approximately 25% seaweed surfactant, 2% clove bud oil, 2% eucalyptus oil, 3% orange and 1% lemongrass. Finally, the athletes foot composition comprises 1 to 3% clove bud oil, 2 to 4% orange, 1 to 3% lemongrass and 12 to 18% anhydrous lanolin. Preferably, however, the athletes foot composition comprises approximately 2% clove bud oil, 3% orange, 2% lemongrass and 15% anhydrous lanolin.

According to a further aspect of the present invention there is provided a method of controlling micro-organisms at a locus, which method comprises applying thereto an effective amount of a composition according to the invention. The term "micro-organism" as defined herein shall be taken to mean any bacteria, virus, fungi or other single/cellular/unicellular or proteinaceous agent capable of transmitting disease or symptoms thereof to an animal or mammal.

The compositions according to the invention have also advantageously been shown to be particularly effective against diseases of poultry such as, for example, Newcastles disease and also against Equine herpes virus. The effective dilution of the composition against equine herpes virus according to the invention may be up to approximately 1 part to 200 parts water.

The present invention may be more clearly understood with reference to the following examples of the invention which are given by way of example only.

EXAMPLE 1

A disinfectant composition comprising (by volume):

| | |
|---|---|
| Eucalyptus Oil | 12.5% |
| Cajuput Oil | 12.5% |
| Clove Bud Oil | 20% |
| Surfactant | 5% |
| Water | 50% | was prepared and tested for its antibacterial efficacy for general orders according to BS6734:1986 as outlined below. The composition passed at a dilution of 1 part disinfectant to 40 parts water tested under the Disease of Animals (Approved disinfectants) Order 1978 as follows:

(a) The effective concentration of the disinfectant is that which when added to the yeast organism mixture gives at least a $10^4$ reduction of bacterial population which determined the effective concentration by the following procedure.

(b) The test was carried out using *Salmonella choleraesuis*, (NCTC* 10653, NCIB# 10383. Stock cultures of the test organism may be stored either as freeze dried ampoules or on nutrient agar slopes, (Oxoid Blood Agar Base) prepared in accordance with "BS 6734:1986, Determination of the Antimicrobial Efficacy of Disinfectants for Veterinary and Agricultural Use". A test culture was prepared by inoculating 10 ml of Oxoid Nutrient Broth No 2 and incubating at 37±1° C. for 24 hours +2 hours. The 24 hour culture should be removed from the incubator immediately prior to use.

*Obtainable from the National Collection of Type Cultures, Central Public Health Laboratory, Colindale, London NW9 5HT.
Obtainable from the National Collections of Industrial and Marine Bacteria Ltd, Torrey Research Station, Aberdeen AB9 8DG.

A yeast suspension (5% dry weight) was prepared in accordance with BS 6734:1986. The suspension was stored at 4±0.5° C. and allowed to age for 6 weeks prior to use. 4 ml of the *S. choleraesuis* test suspension was added to 96 ml of the yeast suspension. 5×2.5 ml portions of the resulting yeast/organism suspension are distributed into 15 mm×150 mm Pyrex test tubes for each disinfectant under test and cooled to 4° C.

A solution of the disinfectant was prepared at 123% in WHO standard hard water (BS 6734:1986) and cooled to 4° C. 10 ml of the cooled disinfectant solution are removed and 2.5 ml added to the first 2.5 ml of the yeast/organism suspension. The resulting mixture was then mixed and the suspension transferred to a fresh cooled test tube. The tube was then incubated at 42 C. for 30 minutes. 10 ml of cooled WHO standard hard water was added to the 123% disinfectant solution to give a second solution with 111% of the recommended use dilution. 10 ml of this was then removed and the test procedure above repeated until 100%, 90% and 81% dilutions of the disinfectant were tested.

After a contact time of 30 minutes, 0.1 ml of the disinfectant/yeast/organism suspension was then added to 10 ml of Nutrient Broth No 2 containing 5% horse serum to inactivate any residual disinfectant. 5×1 ml portions of the inactivated solution were then transferred to 10 ml of Nutrient Broth No 2 recovery broth and the tubes incubated at 37° C. for 48 hours.

After 48 hours the tubes were inspected and the presence or absence of growth is recorded. The final recommended use dilution is the one at which 3 or less tubes out of the 5 inoculated show growth.

EXAMPLE 2

Tables 1 and 2 illustrate the result of the disinfectant test T104 carried out by the Veterinary Laboratories Agency against diseases of poultry (Newcastles disease) at a dilution rate of 1 part disinfectant to 50 parts water. The test is similar to that carried out for general orders disinfectants above except the test organism is Newcastle disease virus, strain "Herts. 1933".

The test mixtures were held at 4° C.±0.5° C. for 30 minutes and at the end of this time a dilution made in 5 percent inactivated horse serum. Further dilutions were made for titrations of the virus in embryonated egg. The disinfectant under test must give a reduction of at least $10^4$ in virus titre.

The test consisted of (a) a toxicity test and (b) a virus test, using 9 day old embryonated eggs.

(a) Toxicity Test (To determine if the disinfectant under test is toxic to embryonated eggs at the lowest dilution to be used in the test ie. at a 1 in 400.
Test Protocol
  i) The disinfectant composition according to Example 1 was prepared using WHO hard water.
  ii) 2.5 ml of the disinfectant was added to an equal volume of a 5 per cent dry weight suspension of yeast prepared as directed in B.S. 808:1938
  iii) After thorough mixing, the test mixture was held at 4° C.+0.5° C. for 30 minutes, shaking at intervals.
  iv) The test mixture was then further diluted 1 in 200 in 5 percent inactivated (56° C. for 30 minutes) horse serum prepared using sterile distilled water.
  (v) 0.2 ml of this dilution was then inoculated into the allantoic cavity of each of, 10 embryonated eggs. Ten control eggs are similarly inoculated with the yeast suspension diluted with an equal volume of hard water.
  (vi) All the eggs were examined daily for 7 days and the disinfectant is regarded as non-toxic if the embryos remain alive at the end of this period.

(b) Virus Test
The test virus is the "Herts 1933" strain of Newcastle disease virus stored at −55° C. The infectivity titre of the virus used must be $10^{9.0}±0.4$ $EID_{50}/0.1$ ml allantoic fluid.

| Test | Controls |
|---|---|
| 1.0 ml virus (allantoic fluid) added to 24.0 ml 5 percent dry weight yeast suspension. | 1.0 ml virus (allantoic fluid) added to 24.0 ml yeast suspension. |
| 2.5 ml yeast-virus mixture added to 2.5 ml disinfectant. | 2.5 ml yeast-virus mixture added to 2.5 ml added to 2.5 ml WHO hard water. |

Both were mixed thoroughly and transferred to fresh container and subsequently held at 4° C.±0.5° C. for 30 minutes with shaking at intervals. They were then diluted 1 in 200 in 5 percent inactivated horse serum in sterile distilled water. Further dilutions were prepared for virus titration in log dilution steps, using 5 percent inactivated horse serum.

Titration in embryonated eggs, using 7 eggs per dilution and inoculating 0.2 ml into the allantoic cavity of each egg and incubating at 37.5° C. was performed.

| Titrate: | Undiluted | Titrate: | $10^{-4}$ dilution |
|---|---|---|---|
| | $10^{-1}$ dilution | | $10^{-5}$ dilution |
| | $10^{-2}$ dilution | | $10^{-6}$ dilution |

All eggs were examined daily for 7 days.

All eggs which die or remain alive after 7 days were tested for the presence of viral haemagglutonin. The titration endpoint was determined by the method of Reed and Muench (1938) Amer. J. Hyg. 27, 493.

To determine drop in infectivity titre, the titre of test material was subtracted from the titre of control material. If this is $10^4$ or $>10^4$, the disinfectant passes if $<10^4$, the disinfectant fails.

The selection, by the VLA, Weybridge, of the dilutions to be tested where a manufacturer only specifies one dilution for a triple dilution test are as follows:

i) If the stipulated dilution is not more than I part disinfectant to 99 parts of water, a tenfold dilution series on either side of the stipulated dilution would be tested eg if stipulated dilution is 1 part to 29 parts water—the test is carried out at the final dilutions of 1 in 20; 1 in 30 and 1 in 40).

ii) If the stipulated dilution is greater than 1 part disinfectant to 99 parts water and not more than 1 part to 250 parts water, a twenty fold dilution series would be tested (eg if the stipulated dilution is 1 part to 149 parts of water the test would be carried out at the final dilutions of 1 in 130, 1 in 150 and 1 in 170.

Disinfectant Test T104

TABLE 1

| Toxicity Test | 1 | 2 | 3 | 4 | 5 | 6 | 7 | 8 | 9 | 10 | Result |
|---|---|---|---|---|---|---|---|---|---|---|---|
| Dilution 1/50 | – | – | – | – | – | – | – | – | – | – | Non-Toxic |
| Control | – | – | – | – | – | – | – | – | – | | |

TABLE 2

| Exposure | Test | 1 | 2 | 3 | 4 | 5 | 6 | 7 | Dead | Titre | Log | Result |
|---|---|---|---|---|---|---|---|---|---|---|---|---|
| Dilution | UD | + | + | + | + | + | + | + | 7/7 | | | |
| 1/50 | $10^1$ | + | + | + | – | – | – | – | 3/7 | | | |
| | $10^2$ | – | – | – | – | – | – | – | 0/7 | | | |
| | | | | | | | | | | $10^{0.93}$ | $10^{4.14}$ | PASS |
| Dilution | UD | | | | | | | | | | | |
| 1/ | $10^1$ | | | | | | | | | | | |
| | $10^2$ | | | | | | | | | | | |
| Dilution | UD | | | | | | | | | | | |
| 1/ | $10^1$ | | | | | | | | | | | |
| | $10^2$ | | | | | | | | | | | |
| Virus | $10^4$ | + | + | + | + | + | + | + | 7/7 | | | |
| Control | $10^5$ | + | + | + | + | – | – | – | 4/7 | | | |
| | $10^6$ | – | – | – | – | – | – | – | 0/7 | | | |
| | | | | | | | | | | $10^{5.07}$ | | |

The disinfectant according to the present example passed the test for approval as a disinfectant for uses against diseases of poultry at a dilution rate of 1 part disinfectant to 50 parts water.

EXAMPLE 3

A disinfectant composition was prepared having the same ingredients as for Example 1 and tested for its effectiveness against Equine herpes virus.

The test method used was that which is provided in Disinfection of Animal Viruses by Evans, Stuart and Roberts (Br vet J 1977, 133, 356), as carried out by the Animal Health Trust (AHT).

| | |
|---|---|
| VIRUS USED IN TEST:~ | EHV 1 (AB4 abortogenic/paralytic strain) |
| CELLS USED IN TEST:~ | RK13 tube cultures. Medium retained during absorption. Cells washed with phosphate suffered saline (PBS) prior to feed. |
| DILUTIONS USED:~ | The disinfectant was dilutated 1/25, 1/50, 1/100, 1/200 and 1/400 in hard water prior to the addition of virus dilutated in yeast solution. |
| RESULTS: | Virus control = 4.50*/per 0.1 ml<br>Disinfectant at 1/25 = <0.75/per 0.1 ml (neat disinfectant toxic to cells)<br>Disinfectant at 1/50 = <0.50/per 0.1 ml (neat disinfectant toxic to cells)<br>Disinfectant at 1/100 = <0.50/per 0.1 ml (neat disinfectant toxic to cells)<br>Disinfectant at 1/200 = <0.50/per 0.1 ml (small cover of cells at base of tube)<br>Disinfectant at 1/400 = 1.75/per 0.1 ml<br>*log to TCID 50 |
| CONCLUSION:~ | Based on the interpretation in the above mentioned publication this disinfectant was efficacious up to a dilution of 1/200. This is the actual dilution of disinfectant prior to the addition of virus in yeast. |

EXAMPLE 4

A range of essential oils were tested for their antimicrobial effects for human application as follows:

1) Antiseptic Mouth Wash and Mouth Ulcer relief:

| Gargle using: | Clove Bud | 2% |
| | Eucalyptus | 2% |
| | Surfactant | 2% |
| | Water | 94% |

The formula is an effective hygienic mouth wash and treatment for mouth ulcers. For mouthwash, gargle using 5 mls of formula mixed with 25 mls water once daily preferably first thing in the morning. For mouth ulcers using a cotton bud, soak formula and gently dab directly over the ulcer. Repeat no more than four times daily.

2) Cold Sore relief:

| Cream using: | Clove Bud | 20% |
| | Tea Tree | 10% |

This highly effective cream should be used as soon as sensation begins. This will prevent the cold sore erupting on the surface of the skin. If the cold sore is already painful and exposed cover the cold sore area only with the cream and gently massage in. Wash hands thoroughly after use. Apply three/four times daily.

3) Head Lice Control:

| Lotion using: | Eucalyptus | 4% |
| | Cajaput | 2% |
| | Clove Bud | 4% |
| | Surfactant | 3% |

The formulation can be made into a shampoo or lotion. Either application needs to be left on the scalp for approximately three minutes and rinsed thoroughly. Kills lice and destroys eggs. Stuck on eggs can be removed using a nit comb. It has been found that if the formula is diluted 1:20 and sprayed sparingly directly onto the hair, this acts as an. excellent repellent.

4) Thrush

| Douche using: | Clove Bud | 15% |
| | Lavender | 3% |
| | Tea Tree | 5% |
| | Surfactant | 5% |

This formula has only been tested on vaginal thrush and was found to be effective. Add 50 mls of formula to 1 litre of warm water and mix well. The mixture can be applied direct or used in a bidet.

5) Verruca cream:

| Cream using: | Clove Bud | 20% |
| | Cajuput | 10% |
| | Lemongrass | 15% |

Mix to a cream base or use as a liquid dab on. Cream and liquid versions work equally as well. Apply a small amount directly over the verruca three times daily. Keep the area clean. Cover with a small plaster after the verruca has been treated. Wash hands thoroughly after use.

6) Wart lotion:

| Lotion using: | Clove Bud | 10% |
| | Lemongrass | 15% |
| | Tea Tree | 5% |

A liquid formula was found to be more effective against warts. Apply by dabbing a small amount of formula directly over wart. Allow to dry. Apply three times daily.

7) Bactericidal Surface Cleaner (Virucidal):

| Spray using: | Seaweed Surfactant | 25% |
| | Clove Bud | 2% |
| | Eucalyptus | 2% |
| | Orange | 3% |
| | Lemongrass | 1% |

The formula was found to be a highly effective surface cleaner around the kitchen. Work surfaces, hobs, ovens, microwaves, fridges and ceramic flooring all came up very clean using the spray and wipe method. To clean tiled floors—just 100 mls in a bucket of water is sufficient. Kills all known bacteria and fungi and contains virucidal activities.

8) Athletes Foot Cream:

| Massage lotion: | Clove Bud | 2% |
| | Orange | 3% |
| | Lemongrass | 2% |
| | Anhydrous Lanolin BP | 15% |

The formula was found to be an effective fungicidal cream against athletes foot where the condition was severe and the skin was cracked and painful. Apply the lotion directly to the affected area and massage well into the skin once or twice daily until the problem clears. Dilute the lotion 1:10 parts warm water and use to thoroughly clean round toenails where the minute fungus often lodges.

What is claimed is:

1. An antimicrobial composition comprising approximately, by volume, 16 to 40% eucalyptus oil, 16 to 40% cajeput oil and 32 to 56% clove bud oil.

2. An antimicrobial composition approximately, by volume, from 10 to 15% eucalyptus oil, 10 to 15% cajeput oil, 15 to 25% clove bud oil, 2.5 to 7.5% surfactant and 40 to 60% water.

3. A composition according to claim 2 which composition comprises by volume 12.5% eucalyptus oil, 12.5% cajeput oil, 20% clove bud oil, 5% surfactant and 50% water.

4. A composition according to claim 2, wherein said surfactant is an anionic surfactant.

5. A composition according to claim 3, wherein said surfactant is an anionic surfactant.

6. A composition according to claim 4, wherein said surfactant is selected from the group consisting of alkylarylsulfonates, alkanesulfonates, alcohol ether and alcohol ether sulfonates, polyether carboxylates, olefinsulfonates, -sulfomonocarboxylic esters and phosphorous containing anionic surfactants.

7. A composition according to claim 5, wherein said surfactant is selected from the group consisting of alkylarylsulfonates, alkanesulfonates, alcohol ether and alcohol ether sulfonates, polyether carboxylates, olefinsulfonates, -sulfomonocarboxylic esters and phosphorous containing anionic surfactants.

8. A composition according to claim 6 wherein said surfactant comprises sodium-2-ethylhexyl sulfosuccinate.

9. A composition according to claim 7 wherein said surfactant comprises sodium-2-ethylhexyl sulfosuccinate.

10. A composition according to claim 1 which is further diluted prior to application.

11. A composition according to claim 10 which is diluted by up to 1 part composition to 200 parts water.

12. A composition according to claim 2 for use in controlling Newcastles disease or Equine herpes virus.

13. A method for controlling the presence of micro-organism at a locus, which comprises applying thereto an antimicrobial effective amount of a composition according to claim 1.

14. A method according to claim 13 wherein said micro-organism comprises any of Equine herpes virus or that which is responsible for Newcastles disease.

15. A method for controlling the presence of micro-organism at a locus, which comprises applying thereto an antimicrobial effective amount of a composition according to claim 1.

16. A method for controlling the presence of micro-organism at a locus, which comprises applying thereto an antimicrobial effective amount of a composition according to claim 2.

17. A method for controlling the presence of micro-organism at a locus, which comprises applying thereto an antimicrobial effective amount of a composition according to claim 3.

18. A method for controlling the presence of micro-organism at a locus, which comprises applying thereto an antimicrobial effective amount of a composition according to claim 4.

19. A method for controlling the presence of micro-organism at a locus, whnich comprises applying thereto an antimicrobial effective amount of a composition according to claim 5.

20. A method for controlling the presence of micro-organism at a locus, which comprises applying thereto an antimicrobial effective amount of a composition according to claim 8.

* * * * *